(12) United States Patent
Moonen et al.

(10) Patent No.: US 9,527,799 B2
(45) Date of Patent: Dec. 27, 2016

(54) PROCESS FOR CHOLINE HYDROXIDE

(71) Applicant: TAMINCO BVBA, Ghent (BE)

(72) Inventors: Kristof Moonen, Hamme (BE); Dieter Ulrichts, Sint-Andries (BE); Daan Scheldeman, Waregem (BE)

(73) Assignee: Taminco, Ghent (BE)

( * ) Notice: Subject to any disclaimer, the term of this patent is extended or adjusted under 35 U.S.C. 154(b) by 0 days.

(21) Appl. No.: 14/783,143

(22) PCT Filed: Apr. 10, 2014

(86) PCT No.: PCT/EP2014/057294
§ 371 (c)(1),
(2) Date: Oct. 8, 2015

(87) PCT Pub. No.: WO2014/167065
PCT Pub. Date: Oct. 16, 2014

(65) Prior Publication Data
US 2016/0068476 A1    Mar. 10, 2016

(30) Foreign Application Priority Data
Apr. 11, 2013    (WO) .................. PCT/EP2013/057617

(51) Int. Cl.
*C07C 213/04*    (2006.01)
*C07C 213/10*    (2006.01)

(52) U.S. Cl.
CPC ........... *C07C 213/04* (2013.01); *C07C 213/10* (2013.01)

(58) Field of Classification Search
None
See application file for complete search history.

(56) References Cited

U.S. PATENT DOCUMENTS

| | | |
|---|---|---|
| 2,774,759 A | 12/1956 | Blackett et al. |
| 3,872,170 A | 3/1975 | Bosche et al. |
| 4,294,911 A | 10/1981 | Guild |
| 4,425,202 A | 1/1984 | Sullivan |
| 4,464,461 A | 8/1984 | Guild |
| 4,686,002 A | 8/1987 | Tasset |
| 5,209,858 A | 5/1993 | Heinsohn et al. |
| 6,440,326 B1 | 8/2002 | Maruyama et al. |
| 7,543,592 B2 | 6/2009 | Lee |
| 8,003,587 B2 | 8/2011 | Lee et al. |
| 9,216,944 B2 | 12/2015 | Moonen et al. |
| 2006/0153912 A1 | 7/2006 | Habich et al. |
| 2007/0193708 A1 | 8/2007 | Broucek et al. |
| 2008/0139436 A1 | 6/2008 | Reid |
| 2009/0111726 A1 | 4/2009 | Shang |
| 2014/0329184 A1 | 11/2014 | Moonen et al. |
| 2014/0361217 A1 | 12/2014 | Moonen et al. |
| 2015/0028253 A1 | 1/2015 | Ferguson |

FOREIGN PATENT DOCUMENTS

| | | |
|---|---|---|
| DE | 241 596 A1 | 12/1986 |
| EP | 1 561 747 A2 | 8/2005 |
| FR | 1 171 967 A | 2/1959 |
| JP | S58-021825 A | 2/1983 |
| JP | 59-134752 A | 8/1984 |
| JP | S62-108848 A | 5/1987 |
| JP | S62-178549 A | 8/1987 |
| JP | H01-230549 A | 9/1989 |
| JP | 2002-317193 A | 10/2002 |
| JP | 2002-357908 A | 12/2002 |
| JP | 2015-501798 A | 1/2015 |
| WO | 2006/005692 A1 | 1/2006 |
| WO | 2013/076190 A1 | 5/2013 |
| WO | 2013/077855 A1 | 5/2013 |
| WO | WO 2013/109705 | * 7/2013 |

OTHER PUBLICATIONS

International Search Report for PCT/EP2014/057294 dated Jun. 3, 2014 [PCT/ISA/210].
ASTM D1209; Standard Test Method for Color of Clear Liquids (Platinum-Cobalt Scale) 2016.
International Search Report and the Written Opinion of the International Searching Authority with Date of Mailing Nov. 23, 2012 for PCT/US2011/061826.
International Search Report and the Written Opinion of the International Searching Authority with Date of Mailing Jan. 18, 2013 for International Application No. PCT/EP2012/073337.
International Search Report and the Written Opinion of the International Searching Authority with Date of Mailing Sep. 14, 2012 for International Application No. PCT/IB2011/003185.
USPTO Office Action dated Oct. 27, 2015 in co-pending U.S. Appl. No. 14/359,508.
USPTO Office Action dated Apr. 28, 2016 in co-pending U.S. Appl. No. 14/359,440.
Response to Communication pursuant to Rule 161(1) EPC dated Feb. 4, 2015 in European Patent Application No. EP12801483.4.
USPTO Office Action dated Aug. 3, 2016 in co-pending U.S. Appl. No. 14/359,508.

* cited by examiner

*Primary Examiner* — Sudhakar Katakam
*Assistant Examiner* — Jennifer C Sawyer

(57) ABSTRACT

Disclosed is a process for the production of choline hydroxide includes reacting at a temperature above 30.0° C. ethylene oxide, trimethylamine, and water in the presence of an aqueous medium in such amounts as to form a diluted choline hydroxide solution having a choline hydroxide concentration of less than 40 wt % and removing at least a portion of the aqueous medium from the diluted choline hydroxide solution to form a concentrated aqueous choline hydroxide solution having a choline hydroxide concentration which is at least 1.05 times the choline hydroxide concentration of the diluted choline hydroxide solution. The process allows for large scale, continuous production of concentrated aqueous choline hydroxide solutions of good quality under economically advantaged consumption factors for ethylene oxide.

31 Claims, No Drawings

PROCESS FOR CHOLINE HYDROXIDE

CROSS REFERENCE TO RELATED APPLICATIONS

This application is a National Stage of International Application No. PCT/EP2014/057294, filed on Apr. 10, 2014, which claims priority from European Patent Application No. PCT/EP2013/057617, filed on Apr. 11, 2013, the contents of all of which are incorporated herein by reference in their entirety.

FIELD OF THE INVENTION

The invention relates to processes for the production of concentrated aqueous choline hydroxide solutions. More particularly the invention relates to a process which may avoid some of the safety risks associated with ethylene oxide as a reactant, and which produces a lower colour product containing less by-product.

BACKGROUND OF THE INVENTION

Choline hydroxide, choline base and in short also "cbase", are terms which are used in this document interchangeably. Choline hydroxide or choline base is also known as 2-hydroxyl ethyl trimethyl ammonium hydroxide or under IUPAC nomenclature rules 2-hydroxy-N,N,N-trimethylethanaminium. The substance is a strong yet organic base, which is an important element for its selection into many end-use applications. Choline hydroxide has applications in the production of other choline salts, for example, by neutralization with an appropriate acid and in applications where a strong base containing very low levels of inorganic ions is needed or where only very low levels can be tolerated. Choline hydroxide is important in a range of applications, such as in the manufacturing of electronics.

Choline hydroxide may be manufactured in a variety of different ways. For example, choline hydroxide may be produced from choline halides (e.g. choline chloride), choline hydroxide may be formed by treating choline sulphate with $Ba(OH)_2$, or choline hydroxide may be produced from a direct reaction.

Choline hydroxide may also be produced by the direct reaction of trimethylamine (TMA), water, and ethylene oxide (EO). U.S. Pat. No. 2,774,759 discloses in example 2 the reaction of 236 parts of a 25% aqueous TMA solution with 40 parts of EO. The mixture is stirred until the reaction is substantially complete, while the reaction temperature is kept below about 30° C. Unreacted TMA is removed under vacuum at about 45-55° C., according to U.S. Pat. No. 2,774,759 leaving cbase in a 40-45% aqueous solution. Assuming ideal 100% selectivity in the reaction and in the TMA removal, one may calculate a product containing 40.65% wt cbase in water. The applicants repeated this experiment, found that the reaction is very slow under these conditions and that it was difficult to remove the excess TMA from the reaction product. The applicants obtained a cbase solution containing 38.5% wt choline hydroxide and 2.2% wt higher-ethoxylated by-products.

This direct method has the advantage of being much more atom efficient as compared to other methods, such as those involving a choline halide starting material. However, the direct reaction of EO and TMA in the absence of a strong acid (e.g. HX) also has some disadvantages.

The ethoxylation of TMA is typically performed in batch mode. Typical is the use of so-called loop reactors, a.k.a. pump-around reactors, whereby the reaction mixture is continuously pumped around from the reactor vessel over a heat exchanger, in order to effectively remove the reaction heat and to keep the reaction temperature low. In order to avoid excessive EO partial pressures, the EO is typically added gradually as the reaction proceeds. In order to drive the consumption of TMA towards completion, an overall molar excess of EO is typically supplied. Any excess of EO, however, will be consumed in O-ethoxylation and form the less desired O-ethoxylates as by-products. When the reaction is approaching completion, it may take up to 10 moles of EO in order to convert 1 further mole of TMA.

A first problem of this reaction path is mainly due to the nature of the trimethylamine (TMA) reactant. Firstly, it is fairly volatile, having an atmospheric boiling point of about 3° C. TMA has a strong and unpleasant fishy odour, and its smell threshold in air is as low as 2 parts per billion (ppb, $10^{-9}$). Vapour by-product streams containing TMA must therefore be incinerated before release, and this should be done at high temperatures to avoid formation of nitrosamines. This poses particular problems when the process involves vacuum conditions. These properties of TMA further impose that the choline product should end up being substantially free of unreacted TMA reactant. Removal of any remaining TMA from the reaction product by stripping with inert gas is unpractical because of its low atmospheric boiling point, meaning it is very difficult to condense from a mixture with an inert gas.

Another problem with the nature of TMA is that it has a limited solubility in water. Excessive presence of TMA will lead to the formation of a separate liquid phase, and not lead to a higher presence of the TMA reactant in the water phase where the reaction occurs. It is thus facing a disadvantage in its competition against cbase product for the addition of an EO molecule.

A second problem of the ethoxylation of TMA to produce choline is due to the nature of the ethylene oxide (EO) reactant. EO is highly reactive, extremely flammable and toxic, and it is rather volatile, having an atmospheric boiling point of about 11° C. EO furnishes its own oxygen for a combustion. Autopolymerisation, with high release of energy, may readily be triggered by a wide variety of factors, even in an inert atmosphere. The reaction is rather impossible to control, usually associated with an explosion. Separate vapour phases containing EO as part of the process are therefore preferably avoided. High partial pressures of EO in such vapour phases should definitely be avoided because of the explosion risk.

A third problem is due to the nature of the choline hydroxide product. Because of the strong basic nature of choline hydroxide, the molecule is prone to side product formation via O-ethoxylation and to colour formation and degradation, for example due to Hofmann elimination during the synthesis.

Because choline hydroxide has a base strength similar to NaOH, it is able to activate its own hydroxyl groups, resulting in an important competition between N- and O-ethoxylation during the synthesis reaction. In the case of N-ethoxylation, a TMA molecule reacts with an ethylene oxide molecule, resulting in the desired choline molecule. In the case of O-ethoxylation, the hydroxyl group of a choline molecule reacts again, with one or more other EO molecules, resulting in choline-like molecules having a higher degree of ethoxylation. The O-ethoxylated by-products still behave as a base, but have lower strength and a higher molecular weight. In many applications they represent impurities in the final product. Furthermore, in many applications, such as the production of choline salts, the molarity (usually expressed in mole/liter) of the hydroxide ion is important and therefore each molecule of EO spent on O-ethoxylation represents an economical loss. The degree of formation of O-ethoxylated products which is observed during the choline hydroxide synthesis may be dependent on the base strength of the solution, and hence upon the hydroxide (here primarily the choline hydroxide) concentration. Apart from the concentration, undesired O-ethoxylation may also be increased by higher reaction temperatures.

Furthermore, choline hydroxide is known to be unstable and to develop colour during synthesis and storage, due to decomposition. Decomposition may occur via a so-called Hofmann elimination, resulting in the formation of TMA and acetaldehyde. Liberated TMA leads to odour problems, such as explained above for unreacted TMA left in the choline product. Acetaldehyde ultimately leads to heavily coloured condensation products, causing concentrated choline hydroxide solutions to become brown and black in a matter of a few days at room temperature. Hofmann elimination reactions are favoured by higher temperatures, and the temperature is therefore preferably kept low during the synthesis of choline hydroxide, in order not to obtain a product already heavily coloured immediately after its preparation.

Colour formation is often prevented by the use of very low process temperatures, as low as in the range of 0° C. to 30° C. Although the reaction between TMA and ethylene oxide is strongly exothermic, the liberated reaction heat can at such low temperatures not be recovered efficiently and economically. Furthermore, keeping the reaction temperature of this exothermic reaction below 40° C. poses a challenge in a large scale process, as the temperature of ambient cooling water is usually insufficiently low and the use of powerful and costly cooling equipment would be required. So, the use of lower reaction temperatures requires an additional input of energy instead of a recovery of reaction heat. Moreover, to guarantee acceptable colour over a prolonged period of time during storage, a stabilizer is often added to the choline hydroxide solution after production.

DD 241596 A1 is concerned with avoiding the flash back of the reactor pressure into the EO railcar container. The document discloses how, using pump-around reactors, in a first reaction step a 25-, 40-, or 50% aqueous TMA solution, from one particular vessel selected from a battery of similar vessels, is reacted with gradually added EO in a primary reaction loop at a temperature of 50-60° C., during which the TMA concentration reduces and the cbase concentration increases, until 80-95% of the required EO has been administered. The further conversion of the remaining TMA is performed by circulating the content of that same vessel over a secondary reaction loop, whereby the temperature is kept at 10-15° C., preferably 12° C., under further addition of EO. The excessive EO which may be present in a small amount is subsequently removed by a short application of a vacuum. The reaction of DD 241596 A1 starts with an at least 25% weight TMA solution, which leads after reaction in the first step to a cbase solution of at least 35.7% wt, and after the second step to a cbase solution of at least 40% wt after removal of the excess EO. This two-step batch process leaves something to be desired in terms of by-product and colour formation at the high cbase concentrations practiced in both steps, and in terms of efficient use of reaction volume and energy.

Thus, there remains a need for an effective and efficient process with efficient and low cost heat control and efficient heat recovery for producing choline hydroxide without undesired by-products and colour formation.

SUMMARY OF THE INVENTION

The present invention includes a process for the production of choline hydroxide and a product obtainable by this process. For example, the present invention relates to a process which allows for large scale production of concentrated aqueous choline hydroxide solutions in good quality under economically acceptable conditions. In particular, the process may include continuous processes for the synthesis of good quality choline hydroxide.

In an embodiment, the invention provides a process for the production of choline hydroxide comprising:
a) reacting at a temperature above 30.0° C., in the presence of an aqueous medium, primary reactants comprising ethylene oxide, trimethylamine, and water to form a diluted choline hydroxide solution having a choline hydroxide concentration of less than 40 wt %, and
b) removing at least a portion of the aqueous medium from the diluted choline hydroxide solution to form a concentrated aqueous choline hydroxide solution having a choline hydroxide concentration which is at least 1.05 times the choline hydroxide concentration of the diluted choline hydroxide solution.

The applicants have found that performing the reaction of step a) at the specified low concentrations of choline hydroxide or "cbase", strongly reduces the formation of O-ethoxylation by-products, in favour of the desired N-ethoxylation of TMA, and at the same time also reduces the tendency for cbase product to undergo degradation reactions, and hence the tendency to develop colour, and this in spite of performing the reaction at the specified relatively high temperatures. Performing the reaction of step a) at the higher temperatures above 30.0° C. brings the advantage of a higher reaction rate, which allows for a more volume-efficient use of the available reactor volume, and thus in a higher throughput for reaction equipment of a predetermined size.

The first difference of the process according to the present invention with the example 2 of U.S. Pat. No. 2,774,759 is that the reaction step forms a diluted choline hydroxide solution having a choline hydroxide concentration of less than 40 wt %. The applicants have found that this lower concentration strongly reduces the formation of O-ethoxylation by-products, and this in favour of the desired N-ethoxylation of TMA.

The applicants have further found that this advantage of higher selectivity may be maintained even when performing the reaction step at a temperature above 30.0° C. This brings a second difference of the process according to the present invention with the example 2 of U.S. Pat. No. 2,774,759, i.e. that the reaction step is performed at a significantly higher temperature. This brings the additional advantage of a higher reaction rate. The applicants have found that the reaction temperature of above 30.0° C. reduces the challenge of maintaining the desired reaction temperature. The higher reaction temperature allows the cooling of the reaction mixture with more conventional means, in many locations possible by cooling with ambient air or an open water cooling system, thereby reducing and possibly even avoiding the need for any complex cooling systems, the investment and the operation costs thereof being rather high. At even higher reaction temperatures, the process according to the present invention presents opportunities for effectively reusing the reaction heat in an application where suitable heating may be required. This advantage may thus represent a reduction of the overall heating duty to be supplied from other sources, and hence represents an increase of the overall energy efficiency. The present invention therefore also represents a significant advantage in terms of complexity and cost for installing and for operating the process, in particular when compared to the process disclosed in U.S. Pat. No. 2,774,759.

The applicants have found that the higher reaction temperature of the process according to the present invention, thanks to the higher solubility of TMA in water at higher temperatures, also allows the reaction to proceed with a higher excess of TMA without the reaction mixture risking to separate into different liquid phases. The applicants have found that this possibility to effectively operate the reaction at a higher excess of TMA represents a further advantage in terms of reaction rate as well as in the selectivity to the desired N-ethoxylation, thereby further enhancing the advantage of a more volume-effective use of reaction volume as well as achieving a higher efficiency of raw material use and higher product purity.

The process according to the present invention may provide for the preparation, for instance at a temperature above about 50° C., of a diluted aqueous choline hydroxide solution containing less than 40 wt % cbase, which is subsequently concentrated (e.g. to about 40%-50% concentrated aqueous choline hydroxide solutions), whereby all process steps may be performed with efficient and low cost heat control and efficient heat recovery. In accordance with an embodiment of the invention, the O-ethoxylation products may also be kept at a level below 10%, below 5%, or below 1% (relative to choline hydroxide) in order to obtain economically advantaged consumption factors for ethylene oxide. Additionally, the process in accordance with the present invention may keep the colour of freshly synthesized, concentrated 40%-50% aqueous choline hydroxide solutions below, for example, about 200 APHA, while using a process temperature above about 50° C., for example.

According to one aspect of the invention, a process for the production of choline hydroxide includes first reacting, in the presence of an aqueous medium, primary reactants comprising ethylene oxide, trimethylamine, and water, to form a diluted choline hydroxide solution. Subsequently, a portion of the aqueous medium is removed from the diluted choline hydroxide solution to form a concentrated aqueous choline hydroxide solution. In one embodiment, the aqueous medium comprises an excess of water and, optionally, an excess of trimethylamine.

Aspects of the present invention may also include the production of a choline hydroxide solution which has a low APHA colour value, e.g. of less than about 200 at room temperature and/or a stabilized choline hydroxide solution, for example, which includes a stabilizer, such as a dithionite salt and/or a dialkyl hydroxyl amine.]

DETAILED DESCRIPTION OF THE INVENTION

As used herein and in the claims, the terms "comprising" and "including" are inclusive or open-ended and do not exclude the presence of additional unrecited elements, compositional components, or method steps. Accordingly, the terms "comprising" and "including" encompass the more restrictive terms "consisting essentially of" and "consisting of." Unless specified otherwise, all values and ranges provided herein include up to and including the endpoints given, and the values of the constituents or components of the compositions are expressed in weight percent or % by weight of each ingredient in the composition. Additionally, each compound used herein may be discussed interchangeably with respect to its chemical formula, its chemical name, a suitable abbreviation, etc.

As used herein, the concentration of choline hydroxide in a composition is meant to comprise not only the choline hydroxide per se, i.e. strictly the 2-hydroxyl ethyl trimethyl ammonium hydroxide itself, but it is meant to also include all the by-products formed by the O-ethoxylation of choline hydroxide into higher molecular weight ethoxylates, regardless of the number of EO molecules which have been incorporated into the molecule.

In an embodiment of the present invention, the aqueous medium comprises water. Water brings the advantage that it is widely available in a quality which is suitable for many of the cbase applications. A further advantage of the use of water as the aqueous medium is that, when water and TMA are removed from the reaction product by means of evaporation, that by appropriately selecting the pressure, the water may readily be condensed at very convenient condensation temperatures, whereby the vapour phase enriches in TMA. This is a major advantage as compared to when TMA is removed from the reaction product by stripping with an inert gas. This advantage may be further exploited such that also TMA may readily be condensed. The TMA vapour may be condensed together with water vapour, resulting in a liquid mixture of TMA and water. The advantage of the process according to the present invention is that at least part of such liquid mixture of condensed TMA and water may be recycled to the reaction step a) of the process.

A further advantage of the present invention, and in particular the use of water as the reaction medium, is that the process according to the present invention is able to produce high purity cbase product, i.e. a cbase product having a reduced content of non-volatile components, which may sometimes be addressed as the "ash" content of an aqueous composition, in particular representing a low metal content.

In more sensitive applications, it may be necessary to use as raw material at least partially and preferably entirely a higher quality water ingredient. In one embodiment, demineralised water may be used and may provide a cbase product having a significantly reduced content of non-volatile components. Applications exist however for which the cbase product made with demineralised water is considered still insufficiently pure. In such instances, a higher purity water quality may preferably be used as the starting material.

According to an embodiment of the invention, a process for the production of choline hydroxide includes reacting, in the presence of an aqueous medium, primary reactants comprising ethylene oxide, trimethylamine, and water to form a diluted choline hydroxide solution (e.g. an aqueous solution of 10 to less than 40% choline hydroxide comprising water as a major part of the balance, such as comprising 90-60% water) removing at least a portion of the aqueous medium from the diluted choline hydroxide solution to form a concentrated aqueous choline hydroxide solution (e.g. a 40-50% aqueous solution of choline hydroxide comprising water as a major part of the 60-50% balance).

In an embodiment of the process according to the present invention, the aqueous medium comprises a molar excess of water of 100% to 6000% relative to the stoichiometric amount theoretically required for forming the amount of choline hydroxide in the diluted choline hydroxide solution, preferably at least 500%, more preferably at least 1000%, even more preferably at least 2000%, yet more preferably at least 2500%, and optionally at most 5000%, preferably at most 4000%, more preferably at most 3500%, yet more preferably at most 3000% relative to the stoichiometric amount theoretically required for forming the amount of choline hydroxide in the diluted choline hydroxide solution.

In an embodiment of the process according to the present invention, the diluted choline hydroxide solution produced in step a) comprises choline hydroxide at a concentration of 10% to 39.0% by weight, based on the total weight of the diluted choline hydroxide solution, preferably at most 38.0%, more preferably at most 37.0%, even more preferably at most 35.0%, yet more preferably at most 32.0%, preferably at most 30.0%, more preferably at most 28.0%, even more preferably at most 26.0%, yet more preferably at most 24.0%, preferably at most 22.0%, more preferably at most 20.0% by weight, and optionally at least 10.0%, preferably at least 15.0%, more preferably at least 18% by weight, based on the total weight of the diluted choline hydroxide solution.

Choline hydroxide, also known as (2-hydroxyethyl)trimethyl-ammonium hydroxide, is an organic base suitable for many uses. For example, aqueous solutions of choline base are useful in connection with electronic applications, such as positive photoresist developing agents, stripping photoresists, anisotropic etching agents, and washing agents for silicon wafers. These electronic applications belong to the highly demanding applications, and may insist on the very low non-volatile content specified elsewhere in this application, in particular on a content of the metals belonging to the group consisting of Fe, Cr, Na, Al, Ca, Cu, K, Mg, Mn, Pb and Zn which is at most 1000 ppb, preferably at most 500 ppb and more preferably at most 200 ppb, and optionally combined with a total metal concentration which is at most 5.0 ppm by weight, preferably at most 2.0 ppm, more preferably at most 1.0 ppm.

In another embodiment, the sodium (Na) content of the cbase produced by the process according to the present invention is at most 1000 ppb by weight, preferably at most 500 ppb.

In an embodiment of the process according to the present invention, the water added to step a) is at least partly comprising but preferably entirely consisting of water having a total metal concentration which is at most 5.0 ppm by weight, preferably at most 2.0 ppm, more preferably at most 1.0 ppm, whereby preferably the sodium content is at most 1000 ppb by weight, preferably at most 500 ppb, and optionally the total content of the metals belonging to the group consisting of Fe, Cr, Na, Al, Ca, Cu, K, Mg, Mn, Pb and Zn is at most 1000 ppb, preferably at most 500 ppb and more preferably at most 200 ppb.

In the context of the present invention, metals as a group are defined as the elements which appear in the IUPAC periodic table of the elements, the version of 22 Jun. 2007 and wherein the element groups are numbered from 1 up to and including 18, in the groups indicated with numbers 1, 2, 3, 4, 5, 6, 7, 8, 9, 10, 11, 12, 13, 14 and 15, excluding hydrogen (H), and which are ranked in that periodic system left of the semi-metals or metalloids, which semi-metals are found on a diagonal line from boron (B) to astatine (At). In the context of the present invention the semi-metals or metalloids, ranked on the diagonal from B to At, are included in the meaning of metals.

In another embodiment, the sodium (Na) content of the water added to step a) is at most 800 ppb by weight, preferably at most 300 ppb.

In another embodiment, the water added to step a) is having at least one and preferably all of the following features:
(i) a concentration of iron (Fe) of at most 200 ppb by weight,
(ii) a concentration of sodium (Na) of at most 200 ppb by weight,
(iii) a concentration of calcium (Ca) of at most 100 ppb by weight,
(iv) a concentration of magnesium (Mg) of at most 50 ppb by weight,
(v) a concentration of potassium (K) of at most 50 ppb by weight.

Because the cbase product and some by-products contain water, there is a need for make-up water into the process according to the present invention. The quality of the water make-up affects the quality of the cbase product, in particular in terms of metal content. The applicants have found that for the production of high quality cbase product, such as the electronic grades discussed above, very high quality make-up water needs to be provided. The applicants have found that the conventional demineralisation techniques are unable to provide the very high water quality required for such high quality cbase product. The applicants prefer to use so-called "polished" water as make-up water to step a) in the production of the high quality low-metal content cbase product described hereinabove.

Choline hydroxide may be produced by the direct reaction of ethylene oxide (EO), trimethylamine (TMA), and water, which may be depicted as follows:

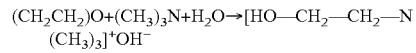

In a process according to the invention, in a first step, ethylene oxide, trimethylamine, and water, the primary reactants, are reacted in the presence of an aqueous medium to form a diluted choline hydroxide solution. In other words, the primary reactants, including ethylene oxide, trimethylamine, and water, may be introduced into a reaction zone to form a reaction mixture. The primary reactants may be added as the starting materials sequentially or simultaneously to the reaction zone, for example, in a continuous manner.

The direct synthesis of choline hydroxide may be performed in a suitable solvent. In other words, the reaction typically occurs in a reaction medium. The reaction medium preferably comprises an aqueous medium. An aqueous medium may comprise an aqueous based solvent, such as water or water miscible alkanols (e.g. methanol) or other solvents (e.g. acetone, acetonitrile, dimethyl formamide (DMF), N-methylpyrrolidone (NMP), dimethyl sulphoxide (DMSO), and the like), for example. For example, a water/methanol mixture may be used as a medium to react EO and TMA. Methanol (MeOH) is more easily removed by volatilization than water. Accordingly, one of ordinary skill in the art may choose the proportions of water and methanol such that after evaporation of all the methanol (and perhaps part of the water that may be co-evaporated), the remaining solution reaches the desired concentrated aqueous choline hydroxide solution (e.g. 40-50% aqueous solution). The synthesis of choline hydroxide may advantageously be performed in an aqueous medium, such as water, which acts both as reagent and as an efficient solvent for the reaction. Preferably, the aqueous reaction medium remains as a continuous, single phase reaction medium throughout the reaction step a). The preferred aqueous medium is water, and the water may be of any suitable type, e.g. distilled, deionized, treated, etc. Preferably, the water is in pure form with little to no impurities.

In an exemplary embodiment, the reaction medium is excess water or an excess of water (e.g. the primary reactants are reacted in the presence of more water). For example, the amount of water present in the first step may include a combination of (i) an amount of water that reacts to form choline-OH (e.g. a stoichiometric amount of water), (ii) an amount of water to make up to the final concentrated solution (e.g. a 45% concentration), and (iii) an amount of water to dilute the choline hydroxide solution in the first step (and which is removed in the second step). The amount of water identified as (iii) may also be characterized as "dilution excess." In other words, the dilution excess includes an amount of water necessary for dilution, which is greater than the amount of water necessary for the concentrated form. The dilution excess may be equal to the amount that would be subsequently removed in the removal (second) step, for example, via evaporation. Therefore, the terms "excess" or "molar excess" may include an amount of typically one reactant, such as water or TMA, which is present above and beyond the stoichiometric amount necessary for the formation of choline, or in other words more than the stoichiometric amount of 1:1:1:EO:TMA:water, and which may include an amount of reactant necessary to form a diluted aqueous choline solution, such as an amount of water or TMA more than what is necessary to form the concentrated aqueous choline solution. The excess water is preferably sufficient to produce a diluted choline hydroxide (e.g. a 10-40% aqueous solution of choline hydroxide comprising water as most of the balance, such as 90-60% water). The excess water may act as a diluent during the reaction, and may thus moderate the temperature increase which may occur locally in parts of the reactor volume, and may also prevent to a large extent the occurrence of degradation reactions and O-ethoxylation reactions. Preferably, the amount of excess water is present in an amount suitable to maintain a single phase continuous reaction medium.

In an embodiment, the excess water may be characterized as "a molar excess" of water (e.g. more water than what is needed for the stoichiometry of the reaction to produce choline hydroxide, which includes an amount of water necessary to form a desired, diluted solution). The molar excess of water preferably includes the dilution excess, which is based on a given concentration of a diluted choline hydroxide solution. The excess water may comprise up to about 7000% molar excess water relative to a stoichiometric amount for a given diluted choline hydroxide solution (e.g. about 1000 to about 6000% may be used, preferably between about 1000% and about 3000%). When more excess water is used, the obtained choline base solution will be more dilute as depicted in Table 1.

TABLE 1

| % cbase | molar excess water | % molar excess of water |
|---------|-------------------|------------------------|
| 45      | 8.2               | 820%                   |
| 40      | 10.1              | 1010%                  |
| 30      | 15.7              | 1570%                  |
| 20      | 26.9              | 2690%                  |
| 10      | 60.5              | 6050%                  |

As one example, a 20% choline hydroxide solution, the dilute solution, may be formed in the first step using a 2690% molar excess of water. Subsequently, in the second step, the dilution excess of water is removed to provide for a 45% choline hydroxide solution.

In an alternative embodiment, the reaction medium further comprises excess trimethylamine (TMA) (e.g. the primary reactants are reacted in the presence of excess TMA). In an embodiment of the process according to the present invention, the reaction medium comprises a molar excess of TMA (e.g. more TMA than the stoichiometric ratio of 1:1:1 molar of EO:TMA:water). Preferably, the amount of excess TMA is present in an amount suitable to maintain a single phase continuous reaction medium. Without wishing to be bound by a particular theory, it is believed that the competition between O- and N-ethoxylation during the synthesis of choline hydroxide may also be controlled to a certain extent by using an excess of TMA in the reaction medium. This factor is exploited in the conventional so-called "fed batch" processes, wherein ethylene oxide is fed gradually to a batch of a pre-mixture of water and excess TMA present in the reactor. In the fed batch process, a very high excess of TMA is present during the early stages of the reaction, with O-ethoxylated products being formed mainly towards the end of the EO addition, as the reaction reaches completion, most TMA is consumed, and also the concentration of hydroxide ions is at its highest. This stoichiometric effect, together with the careful temperature control necessary for ethoxylation reactions, explains why the use of a fed batch process is so popular.

The applicants have found that the process according to the present invention may use for step a) also the reaction step which is used as part of the conventional "fed batch" process. The applicants have found that also in such an embodiment, the reaction may advantageously be performed at a temperature above 30.0° C., provided that the reaction step produces a diluted choline hydroxide solution having a choline hydroxide concentration of less than 40° wt %. The applicants have found that also in this embodiment, the effects of higher selectivity and reaction rate, and the improved colour product, may be obtained.

In a fully continuous process, however, TMA and ethylene oxide may be mixed at the overall stoichiometric ratio present at the inlet of the reactor. Therefore, the competition between N- and O-ethoxylation is more constant over time, and typically higher levels of O-ethoxylation, as compared to the fed batch operation, are observed. An excess of TMA may be used to counteract this effect. The excess of TMA may be removed from the final product mixture by evaporation. However, the use of an excess of TMA is limited by the fact that two phases may form in the reaction mixture. The occurrence of two phases is detrimental to process operability because proper mixing may no longer be guaranteed, and the availability to the reaction of at least one of the reactants may become reduced, which may affect reaction rate as well as selectivity.

The amount of TMA excess which causes phase separation to occur is dependent on the choline hydroxide concentration of the mixture. At higher hydroxide concentration of the reaction mixture, TMA solubility is significantly decreased. At a typical commercial product concentration of 45% choline hydroxide, the molar excess of TMA may not be higher than 10% to 20% (meaning 1.1 to 1.2 equivalents of TMA relative to EO) in order to prevent a phase separation from occurring. By working at a higher degree of dilution, according to the present invention, a higher excess of TMA may be tolerated without the formation of two phases, and thereby a better quality product may be obtained, also in a fully continuous process, but also in the fed batch process. When the process is run according to the present invention, an excess of trimethylamine may comprise up to about 200% excess trimethylamine relative to a stoichiometric amount necessary for the reaction (e.g. an excess of TMA between about 0 or 1 up to about 200% may be used, preferably between about 20% and about 100%).

In an embodiment of the process according to the present invention, therefore, the molar excess of trimethylamine is in the range of 5% to 200% excess trimethylamine relative to the stoichiometric amount required for forming the amount of choline hydroxide in the diluted choline hydroxide solution, preferably at least 10%, more preferably at least 20%, even more preferably at least 25%, yet more preferably at least 30%, preferably at least 35%, more preferably at least 40%, even more preferably at least 45%, yet more preferably at least 47%, and optionally at most 150%, preferably at most 120%, more preferably at most 100%, even more preferably at most 80%, yet more preferably at most 70%, preferably at most 60% excess trimethylamine relative to the stoichiometric amount required for forming the amount of choline hydroxide in the diluted choline hydroxide solution. This feature brings the advantage already mentioned before by assuring a single phase reaction medium, in terms of reaction rate and selectivity, as well as in terms of product quality, in particular with lower O-ethoxylation by-products and with a better colour.

The reaction medium may include any suitable reaction medium or combination of mediums, e.g. water and trimethylamine, etc. Without wishing to be bound to a particular theory, it is believed that by selecting an aqueous medium, such as water, as the reaction medium, the highly diluted choline hydroxide solutions are much less prone to colour formation through product degradation and the choline hydroxide solutions may be produced with little or no by-products (e.g. O-ethoxylation products and degradation reaction(s) are minimized).

Other reactants, solvents, catalysts, etc. may also be added with the primary reactants at the start of the reaction or during the reaction, for example, as will be appreciated by one of ordinary skill in the art. Additionally, any pre-treatments, such as pre-treating the water with trimethylamine may also be performed as needed (e.g. in the case where a stabilizer hydrolyzes at a neutral or acid pH).

The reactants and the reaction medium may be of any suitable state (e.g. liquid). In an exemplary embodiment, the entire process is run in the liquid phase. Thus, the reactants and reaction medium may be introduced in the liquid phase, and the products and by-products may be extracted in the liquid phase. For example, the ethylene oxide and TMA may be injected as liquids in a reaction zone with circulating liquid water as the reaction medium. The liquid which circulates as the reaction medium is preferably a continuous, single phase medium. A suitable reactor pressure may be applied in order to keep all reagents and products in the liquid phase. For example, the pressure may be between about 1 and 100 bar, preferably between about 2 and 50 bar, more preferably in the range from 3 to 30 bar, even more preferably from 4 to 15 bar, yet more preferably from 5 to 10 bar, preferably from 6 to 8 bar, whereby these pressures are expressed as bar gauge, i.e. meaning the extra pressure above the pressure of the atmosphere.

The reaction zone may include any suitable means or equipment known in the art to provide the proper reaction conditions. The reaction zone may include a continuous reactor where reactants are continuously fed into the reactor and emerge as a continuous stream of product. For example, the reaction zone may include a continuous reactor, such as a tubular reactor, a multi-tubular reactor, a continuous stirred tank reactor (CSTR), a loop reactor, a plug flow reactor (PFR) (e.g. a vessel through which flow is continuous, usually at steady state, and configured so that conversion of the chemicals and other dependent variables are functions of position within the reactor rather than of time), or any other reactor type known to one of ordinary skill in the art, and the reaction zone may be combinations thereof. In one embodiment of the present invention, the reaction zone is a continuous tubular reactor (CTR), a continuous stirred tank reactor (CSTR), or a hybrid type between the two, or a combination thereof, for example.

It was discovered that the aqueous liquid (e.g. excess water and optionally excess TMA) was found to act as an ideal medium to perform the choline hydroxide synthesis. When ethylene oxide was injected together with a sufficient amount of liquid TMA into water while providing sufficient mixing, choline hydroxide was formed at a high reaction rate. Complete conversion of ethylene oxide may be observed at residence times in the reaction zone as low as 10 minutes. Longer residence times may also be used with no adverse effects. The use of a longer residence time may require the use of larger and more expensive equipment, however. The residence time in the reaction zone therefore preferably is in the range of from 5 to 1000 minutes, more preferably from 7 to 300 minutes, even more preferably from 9 to 200 minutes, yet more preferably from 10 to 100 minutes, preferably from 12 to 75 minutes, more preferably from 15 to 50 minutes, even more preferably from 20 to 45 minutes, yet more preferably from 25 to 40 minutes.

The exothermic reaction enthalpy, also known as the heat of reaction, for the reaction of EO, TMA, and water to form choline hydroxide is 117 kJ/mol EO. Because the reaction is so highly exothermic, the reaction requires careful temperature management. When water, TMA, and EO would be mixed in the required proportions to obtain a 45% aqueous choline hydroxide solution, for example, the temperature would rise to about 200° C. when the heat is dissipated equally through the reaction mixture. According to one aspect of the invention, the reaction is occurring in a diluted form (e.g. in an aqueous medium) and therefore the reaction heat liberated per mole of choline hydroxide formed is dissipated in a larger mass resulting in a reduced temperature increase within an adiabatic reaction zone as compared to the "adiabatic temperature rise" in an undiluted mixture. Water has a high heat capacity (Cp.), which makes water the preferred reaction medium to control the temperature rise during the reaction.

The reaction step is performed advantageously at a temperature between 40° C. and 150° C., more preferably between 50° C. and 100° C. At these temperatures, a good balance between reaction kinetics, product quality (degradation and O-ethoxylation) and process economics may be obtained. For example, the high reaction temperature in the first step may allow for the use of cost efficient cooling methods and for efficient heat recovery (e.g. via heat exchangers).

In an embodiment of the process according to the present invention, the primary reactants are in step a) reacted at a temperature of at least 35° C., preferably at least 40° C., more preferably at least 45° C., even more preferably at least 50° C., yet more preferably at least 55° C., and optionally at most 150° C., preferably at most 120° C., more preferably at most 100° C., even more preferably at most 90° C., yet more preferably at most 80° C., preferably at most 75° C., more preferably at most 70° C., even more preferably at most 65° C. As already mentioned above, the higher reaction temperatures bring the advantage of a higher reaction rate, which allows for a more effective use of the available reaction volume, and/or for a higher throughput for a predetermined reaction volume. A further advantage is an easier removal of the reaction heat, resulting in a simpler and less expensive system to maintain the desired reaction temperature. The higher reaction temperatures may bring the advantage of a possible reuse of the reaction heat in a useful application, possibly replacing another source of heat which may represent an additional operating cost. The higher reaction temperatures bring the further advantage of a higher solubility of TMA in water, hence allows to operate with a higher excess of TMA reactant in the reaction, while this higher amount of TMA remains present in the water phase, where the reaction occurs. In spite of the higher excess of TMA, this TMA remains available for the reaction, rather than separating into a separate liquid phase.

Removal of reaction heat may be achieved by any means known to people of ordinary skill in the art. Heat may be removed by circulating a cooling medium through built-in heat exchangers (e.g. in a loop reactor or a reactor equipped with an internal cooling coil) or around the reactor wall (e.g. double jacketed tubular reactor or stirred tank reactor). Low cost ambient cooling water, as is available at a typical chemical plant (e.g. water extracted from a nearby river or water from a closed loop cooling circuit cooled by cooling towers located in ambient air), is advantageously used as the cooling medium because it may more readily be made available at economically more attractive conditions as compared to its alternatives. Most preferably, the reaction is performed in an adiabatic reactor. In this mode, it is not required to remove any heat during the reaction. The temperature of the reaction mixture may be allowed to increase along the path of the reaction medium through such adiabatic reactor. Moreover, the temperature increase in such an adiabatic reactor preferably does not cause significant deterioration of the product quality. A big advantage of running the reaction in an adiabatic reactor is that heat removal may be carried out more advantageously in a downstream processing step (for example, during removal of excess TMA and/or during concentration of the aqueous solution).

If necessary, the heat may be extracted and/or maintained at any suitable time before, during, or after the reaction. For example, the inlet temperature of the reactants, the temperature of the reaction mixture during the reaction, and the product and by-product streams may be maintained at a given temperature (e.g. above about 50° C.). Without wishing to be bound by theory, by controlling the heat of the reaction mixture, economically acceptable choline hydroxide contents may be achieved and colour formation may be minimized. Additionally, performing the TMA ethoxylation reaction in an aqueous medium allows for the use of higher temperatures in the process. While processes described in the prior art typically work at low temperatures of at most 30° C., to reduce side product formation and degradation, the present invention allows for higher process temperatures while still providing choline hydroxide solutions with acceptably low levels of higher ethoxylates and low colour. In one embodiment, the temperature throughout the process is maintained at a temperature in the range of about 40° C. to about 150° C., about 50° C. to about 150° C., preferably about 50° C. to about 100° C., or more preferably about 50° C. to about 80° C.

The temperature may be maintained using any suitable means known to one of ordinary skill in the art. For example, the heat may be controlled using at least one heat exchanger, and which may be organized in parallel flow, counter flow, and/or cross flow. The heat exchanger may be part of the reaction zone, prior to, and/or subsequent to the reaction zone. For example, the temperature in the reaction zone may be controlled by passing a temperature controlling medium through an external mantle provided on the reaction vessel. By running at a process temperature above 40° C. or above 50° C., for example, the reaction heat may be efficiently removed using readily available ambient cooling water. The collected product streams may also be cooled by passing the streams through a heat exchanger.

The direct synthesis as part of the process according to the present invention forms a diluted choline hydroxide solution. In other words, the aqueous choline hydroxide solution may entrain a significant amount of water from a single phase reaction medium, which contains more water than is strictly required to obtain a concentrated aqueous choline hydroxide solution (e.g. 45% wt choline hydroxide). This results in an aqueous choline hydroxide in diluted form (e.g. a concentration of choline hydroxide of about 10% to about 40% by weight and about 90% to about 60% water, based on total weight of the diluted choline hydroxide solution). For example, the concentration range for diluted choline hydroxide may be between about 15% to about 30% by weight (e.g. about 85% to about 70% water), based on total weight of the dilute choline hydroxide solution. At lower concentrations, the process may become inefficient due to the large amounts of water which must be removed in the second step and also due to the excessively large and expensive equipment required to have an industrially relevant throughput. The diluted choline hydroxide solution resulting from the first step is preferably transparent and generally has low colour. For further improved colour control, a colour stabilizer, such as a sulphite salts, formaldehyde, borohydrides, and/or other stabilizer known in the art, may be added together with the reagents to the reactor, for example.

The diluted choline hydroxide may then be concentrated to a concentration that is suitable for most applications (e.g., a concentration of about 40% to 50% by weight, based on total weight of the concentrated choline hydroxide solution). Thus, in a second step, a portion of the aqueous medium is removed from the diluted choline hydroxide solution to form a concentrated aqueous choline hydroxide solution.

In an embodiment of the process according to the present invention, the concentrated aqueous choline hydroxide solution has a choline hydroxide concentration which is at least 1.10 times the choline hydroxide concentration of the diluted choline hydroxide solution, preferably at least 1.20 times, more preferably at least 1.50 times, even more preferably at least 1.75 times, yet more preferably at least 2.00 times the choline hydroxide concentration of the diluted choline hydroxide solution formed in step a). The applicants have found that the concentration step may be performed such that any effects on product quality remain readily acceptable, and may even be minimized.

In an embodiment of the process according to the present invention, the aqueous medium is at least partially removed from the diluted choline hydroxide solution by at least one of evaporation, stripping, membrane based separation, and combinations thereof, preferably the evaporation at least partly being performed under vacuum, preferably the evaporation followed by at least partial condensation of the evaporated water and possibly present evaporated trimethylamine, more preferably the process further comprising the step of recycling at least part of the condensed water to step a).

The diluted choline hydroxide may be concentrated by any suitable techniques known in the art. For example, concentration of the diluted choline hydroxide solution may be achieved by the removal of at least a portion of the water. The removal of a portion of the aqueous medium, such as water, may be accomplished by any of the known techniques, such as evaporation or membrane based separations (e.g., dialysis, electrodialysis, reverse osmosis, etc.), for example. Evaporation of water may be achieved by any means known to one of ordinary skill in the art, for example, by distillation, flash evaporation, and/or thin film evaporation. Evaporation of water may be performed at atmospheric pressure, for example, but is more advantageously performed at reduced pressure, such that also the temperature may be reduced, in order to obtain low coloured product. For obtaining favourable energy consumption in the evaporation step, techniques such as multistage evaporation and vapour recompression may also be used. When the reaction in the first step of the process is run at sufficiently high temperature, heat may be recovered from the reaction section in the first step a) for use in the evaporation section in the second step b). Shorter contact time and lower temperature in the water removal step may also favour the formation of low colour product. A stabilizer such as a sulphite salt, formaldehyde and/or others known in the art may be added after the first step but prior to evaporation in order to obtain an improved colour product.

When an excess TMA has been used in step a) of the process according to the present invention, the excess trimethylamine is removed from the diluted choline hydroxide solution or from the concentrated choline hydroxide solution. This brings the advantage that a the problem of residual odour of TMA in the cbase product is reduced and preferably even avoided or eliminated.

The aqueous choline hydroxide, in diluted or concentrated form, may also be stripped of excess TMA to yield commercial grade choline hydroxide material. Residual TMA in the choline base product is not desired in most applications, as it imparts a strong fishy smell to the product. Thus, residual TMA may be removed by any of the techniques commonly known to those skilled in the art, such as stripping with an inert gas, boiling off under vacuum, distillation, and so forth.

Moreover, most of the remaining TMA, of the excess in aqueous medium, and/or any residual EO may be separated from the choline hydroxide solution and reintroduced into the reaction zone (e.g. recycled to an inlet of the reaction zone) to be further used as the reaction medium and/or as a reactant. For example, the water may be advantageously recycled to the reaction zone as a reaction medium. In this way, the concentration of choline hydroxide in the reaction zone may be kept so low that O-ethoxylation is significantly disfavoured and the amount of higher ethoxylates found in the final solution is significantly lower than what is typically obtained in the conventional process operating at the higher choline hydroxide concentrations.

The choline hydroxide solution may also include negligible amounts of other by-products (e.g. higher ethoxylates formed by O-ethoxylation). Preferably, the choline hydroxide, in dilute and concentrated form, contains low levels of other significant side products (e.g. below about 10%, below about 5%, or below about 3%), such as O-ethoxylates. When the synthesis of aqueous choline hydroxide solutions is performed as described herein, the amount of O-ethoxylated products may readily be kept below about 10% by weight relative to choline hydroxide. A choline hydroxide solution of 45% with 10% by weight of O-ethoxylation products has consumed 7% more ethylene oxide than is theoretically required for a pure choline hydroxide solution of equivalent hydroxide molarity. Thus, the occurrence of O-ethoxylated products therefore not only represents a possible product quality issue, but also represents an economical loss.

In an embodiment of the process according to the present invention, the diluted choline hydroxide solution comprises O-ethoxylation products at a concentration of at most 10% by weight, based on total weight of the diluted choline hydroxide solution, preferably at most 8.0%, more preferably at most 6.0%, even more preferably at most 5.0%, yet more preferably at most 4.0%, preferably at most 3.0% and more preferably at most 2.0% by weight, based on total weight of the diluted choline hydroxide solution.

In applications where choline hydroxide is used as a base, for instance in the neutralization of a variety of acids in order to obtain the corresponding choline salts, the concentration of hydroxide ions is an important quality parameter. The higher ethoxylates still act as bases, and may participate as active components in those applications, but carry the drawback of a higher molecular weight. Higher ethoxylates also lead to a higher consumption of EO for the same number of hydroxide equivalents produced, and O-ethoxylation thus leads to a significant cost increase in the synthesis of choline hydroxide. Thus, aspects of the present invention result in both better quality choline hydroxide product, with a higher concentration of hydroxide ions for the same concentration by weight of total base, and a significant reduction in raw material cost.

The desired products and/or by-products may be separated, extracted, or purified using any means and equipment known to one of ordinary skill in the art. For example, the products may be separated from each other using distillation, stripping with an inert gas, boiling off under vacuum, and so forth. For example, the choline hydroxide solution may be subsequently treated to remove some or all of the residual reagents (e.g. trimethylamine) or O-ethoxylated side products.

The concentrated choline hydroxide solution may comprise any suitable concentration of choline hydroxide. The concentration of choline hydroxide in the concentrated solution may be high (for example, on the order of about 25 to about 75 weight %, about 30 to about 60 weight %, about 40 to about 50 weight % choline hydroxide, or about 45 weight % choline hydroxide) based on the total amount of the aqueous choline hydroxide solution. In one embodiment, the concentrated choline hydroxide solution comprises choline hydroxide at a concentration of about 40% to 50% by weight, based on total weight of the concentrated choline hydroxide solution.

The diluted and/or concentrated choline solution preferably is produced with a clear or slightly off-colour (e.g. an APHA number of less than 500 and preferably less than 200) appearance at room temperature (e.g. about 20-25° C.) under standard conditions. The colour of the choline solution is preferably evaluated by measuring the American Public Health Association (APHA) colour, for example, following appropriate American Society for Testing and Materials (ASTM) procedures. The applicants prefer to use a method according to ASTM D1209. APHA measurements may be obtained, for example, using a calibrated Lovibond PFX195 Tintometer with a 5 cm path length quartz cell. The APHA colour value represents a scale ranging from a low colour, transparent/light coloured sample to a high colour, opaque/dark colour sample. For example, a value less than 20 may be indicative of a clear or water-white sample, a value less than 100 is indicative of a clear or slightly off-colour appearance sample, a value less than 500 is indicative of a clear to amber sample, and a value greater than 500 is indicative of amber to an opaque dark colour. Thus, a lower value establishes a more clear/lighter sample whereas a higher value designates a more opaque/darker sample. As the darkness and opaqueness represents the presence of degradation reactions and associated by-products of the choline base, a lower value is desired.

In an embodiment of the process according to the present invention, the concentrated aqueous choline hydroxide solution has an APHA colour value of less than 500 at room temperature, preferably at most 400, more preferably at most 300, even more preferably at most 200 at room temperature.

The choline hydroxide solution produced in the process according to the present invention may also be stabilised. The diluted cbase solution may already be stabilised, and most of the stabiliser in the diluted cbase solution may be retrieved and/or retained in the concentrated cbase product. The applicants prefer to add any stabiliser downstream of the reaction step a), more preferably in the already concentrated cbase solution, i.e. after the concentration step b). The applicants have found that this is operationally more easy to achieve. The applicants have also found that this reduces the risk that the concentration step b) is affected by the stabiliser, and the risk that some of the stabiliser ends up in the water and/or TMA which is condensed after step b) and which may discarded and hence lost, or be recycled to the reaction step, where it may affect the reaction itself.

Thus more importantly, the concentrated cbase solution may be stabilised. In an embodiment, the concentrated aqueous choline hydroxide solution comprises a stabiliser. Stabilisation may be obtained by using, preferably adding, any suitable stabilizers known in the art, for example, for the purpose of preventing colour formation and preserving the overall quality of the product. As used herein, the terms "stabilizing" and "stabilized" are intended to encompass a choline hydroxide solution which undergoes minimal or no degradation reactions which would otherwise deteriorate the quality of the choline hydroxide solutions. In other words, there is reduced or no development of heavy/dark colour, formation of precipitates, volatility, a strong smell, etc. Instead, the stabilized choline solution may maintain a clear or slightly off-colour (e.g. APHA of less than 500 and preferably less than 200) appearance for an extended period of time (e.g. at least one week, at least one month, at least three months, etc.) at room temperature (e.g. about 20-25° C.) under standard conditions.

Any suitable stabilizer may be used, including but are not limited to, dithionite salts (e.g. an alkali metal dithionite), amines (e.g. dialkyl hydroxyl amines), sulphites, hydroquinones, hydrides, carboxylic acids, piperazines, formaldehyde, etc., and mixtures thereof. For example, the stabilizer may comprise sodium dithionite, N,N-diethyl hydroxyl amine, ethylene diamine tetraacetic acid (EDTA), methoxy hydroquinone (MEHQ), tetramethyl piperazine-N-oxide (TEMPO), diethylene triamine (DETA), benzaldehyde, sodium sulphite, boric acid, tetraethylene triamine (TETA), sodium borohydride, butylated hydroxyanisole, sodium metabisulphite, ascorbic acid, thiourea, formaldehyde, and mixtures thereof. The stabilizer may be added in any suitable form (e.g. powder, aqueous, or in any form convenient for use in the process of choline hydroxide manufacture) and at any suitable time (e.g., before formation, after formation of diluted solution, or after formation of concentrated solution). For preferred stabilisation techniques and stabiliser compounds, the applicants refer to WO 2013/077855 A1 and WO 2013/076190 A1.

In one embodiment of the invention, a continuous process for the production of choline hydroxide includes reacting ethylene oxide, trimethylamine, and an excess of water to form a diluted choline hydroxide solution; and removing a portion of the water from the diluted choline hydroxide solution to form a concentrated aqueous choline hydroxide solution. Such a process allows for large scale, continuous production of concentrated aqueous choline hydroxide solutions in good quality under economically acceptable conditions. Additionally, the O-ethoxylation products may also be kept at a level below 10%, below 5%, below 2%, or below 1% (relative to choline hydroxide. Additionally, the colour of freshly synthesized, concentrated aqueous choline hydroxide solutions (e.g. 40%-50% concentrations) may be maintained below, for example, about 200 APHA while using a process temperature above 50° C.

In an embodiment, the method according to the present invention is performed in continuous mode. Aspects of the present invention may thus include a continuous process for the production of choline hydroxide. As used herein, the term "continuous" is intended to encompass processes that synthesize choline hydroxide in one or a single continuous process. In other words, the choline hydroxide does not require multiple steps (e.g. synthesizing an intermediate compound or compounds and, for example, in a separate operation, converting the intermediate(s) to choline hydroxide) being performed in the same reactor vessel. The process may be continuous in the sense that at least some of the reactants may be introduced and products withdrawn simultaneously in an uninterrupted manner (e.g. the process does not involve or require the start and stop of separate reaction steps or batches). The continuous process may or may not include the recycling of products, intermediate products and/or by-products (e.g. a choline solution may be recycled to a reaction zone were EO may be constantly fed until the desired concentration is reached). The term "single pass" may be used to indicate that there is no recycling of the particular component or of the product in the process.

In an embodiment, the reaction of step a) of the process according to the present invention is performed in at least one loop reactor. A loop reactor is a reactor in which the reaction medium is continuously circulated. Typically a loop reactor comprises at least one heat exchanger over which the reaction medium is circulated and which withdraws heat from the reaction medium. The circulation of the medium in a loop reactor may be driven by any suitable means, such as by gravity making use of density differences between individual zones in the loop reactor. The circulation in a loop reactor may also be driven by a pump, e.g. withdrawing medium from a reservoir, pushing the medium through the heat exchanger after which at least a major portion of the medium may be returned to the reservoir. The heat exchanger may also be located upstream of the pump, in between the reservoir and the pump. Reagents may be added at various locations in the reactor loop. With a highly exothermic reaction such as the production of choline from TMA, water and EO, the EO may for instance be injected immediately upstream of the heat exchanger, in which case the EO may be gaseous, or in the suction of the pump feeding the heat exchanger, in which case the EO is preferably liquid at reaction conditions in order to avoid pump cavitation problems.

In an embodiment, the reaction step a) of the process according to the present invention is performed in at least two reactors in series, preferably in three reactors in series, meaning that the product of the first reactor is fed to a second reactor, and so forth. This brings the advantage that the upstream reactor may produce an intermediate product still containing significant amounts of unreacted reagents, such as unreacted TMA, which may have another chance of converting in the downstream reactor or reactors. This brings the advantage that the reaction rate may be higher in the upstream reactor or reactors, because of a higher presence of unreacted reagents, and that the selectivity may be favourably affected in the upstream reactor or reactors because of the lower concentration of the reaction product or products.

In an embodiment in which step a) uses more than one reactor, the ethylene oxide (EO) addition is split and divided over more than one of the reactors. This brings the advantage that not all the EO required for the reaction has to travel through the entire train of reactors, which brings an advantage of a more volume efficient reaction zone, hence higher capacity and/or throughput for a predetermined reactor volume. It brings the further advantage that the reaction and the associated generation of reaction heat may be controlled and managed by managing the split and division of the EO feed over the number of reactors.

In an embodiment of the process according to the present invention, the trimethylamine is produced by the reaction of methanol and ammonia, preferably over a solid acid catalyst, more preferably over a silica-alumina catalyst, even more preferably a catalyst selected from an amorphous silica-alumina catalyst and a shape-selective zeolite catalyst.

The concentrated cbase solution produced in step b) of the process according to the present invention may advantageously be used in a variety of ways. In an embodiment, the process according to the present invention further comprises the step of using the concentrated choline hydroxide from step b) for a use selected from the group consisting of the neutralisation of an acid compound, preferably in a formulation, such as a formulation selected from a detergent formulation, an agrochemical formulation, and combinations thereof.

In an embodiment, the process according to the present invention further comprises the step of reacting the choline hydroxide from step a) or from step b) to form an ionic surfactant, preferably a surfactant having the formula R-A-$SO_3^-[(H_3C)_3N$—$CH_2$—$CH_2$—$OH]^+$, whereby A represents an oxygen atom or a group having the formula —$[O-B]_n$-O—, whereby B represents an alkyl group having 2 to 4 carbon atoms and n represents an integer in the range of 1-20, and R represents a saturated or unsaturated, unbranched or branched alkyl group having from 8 to 30 carbon atoms.

The invention is now further illustrated by means of the following examples, without being limited thereto.

EXAMPLES

Example 1

Showing the Effect of Choline Hydroxide Concentration on the Amount of O-Ethoxylates Formed TMA, EO, and water were fed continuously to a 300 ml autoclave by means of a mass flow controller. Product was extracted from the reaction at such a flow rate to keep the liquid level inside the reactor constant. The autoclave was equipped with a magnetically coupled high speed blade stirrer and was heated to the desired temperature by means of an electrical heating mantle. The total flow rate was chosen in such way to have a residence time in the reactor of 20 minutes. The ratio of the TMA/EO/water flow was chosen in such way to obtain an appropriate target theoretical choline base ("cbase") concentration, assuming perfect selectivity of all reactants towards the choline hydroxide product. Samples were taken at regular time intervals and until a stable reactor output was found. The amount of O-ethoxylated products was measured in the samples and expressed as % wt on dry matter (DM) for comparison reasons (meaning disregarding any water and excess TMA present in the samples). The results are listed in Table 2.

TABLE 2

| | Desired Temperature (° C.) | Theoretical cbase Concentration (% wt) | Molar Ratio TMA/EO | Amount of O-Ethoxylated Products (% wt DM) |
|---|---|---|---|---|
| A | 70 | 17 | 1 | 15 |
| B | 70 | 40 | 1 | 21 |

These results show that a higher concentration of cbase leads to a higher level of O-ethoxylation, and the formation of more O-ethoxylated by-products.

Example 2

Showing the Effect of the Use of Excess TMA on the Amount of O-Ethoxylates Formed A set of experiments was performed as described in example 1, in which the molar ration of TMA/EO was varied. The results are given in Table 3.

TABLE 3

| | Desired Temperature (° C.) | Theoretical cbase concentration (% w) | Molar Ratio TMA/EO | Amount of O-Ethoxylated Products (% w DM) |
|---|---|---|---|---|
| C | 50 | 17 | 1 | 11 |
| D | 50 | 17 | 2 | 3 |

These results show that a stoichiometric excess of TMA leads to a lower level of O-ethoxylation, and the formation of less O-ethoxylated by-products.

The comparison of these results with those of Experiment A from Example 1 shows that the beneficial effect of raising the molar ratio TMA/EO from 1:1 to 2:1 may readily outweigh the relatively limited loss of selectivity when raising the temperature from 50° C. to 70° C. Increasing the TMA/EO to advantageous ratios may not be possible at higher cbase concentrations, as this may lead to phase separation. This is illustrated in the next example.

Example 3

Showing that the Beneficial Effect of Using an Excess of TMA May be Exploited at Lower Choline Hydroxide Concentration (about 28.5%)

A set of experiments was performed as described in example 1 with examples E and G performed at a lower choline base concentration of 28.5% and example F performed at a higher choline base concentration of 48%. The results are given in Table 4.

TABLE 4

| Desired Temperature (° C.) | Theoretical cbase concentration (% wt) | Molar Ratio TMA/EO | Amount of O-ethoxylated Products (% wt DM) |
|---|---|---|---|
| E | 60 | 28.5 | 1.5 | 6 |
| F | 60 | 48 | 1.5 | * |
| G | 60 | 28.5 | 2.3 | * |

*Phase separation occurred and no stable product composition could be obtained from the continuous reactor upon repetitive sampling.

These results show that high TMA presence as well as high cbase concentration leads to a separation of the reaction mixture into two liquid phases. Phase separation limits the availability of some of the reactants in some of the phases, which may impact selectivity and reaction rate, usually in a negative sense.

Example 4

Showing Production of 45% Choline Hydroxide Solution without Stabilizer

A sample of aqueous choline hydroxide (25% wt) was prepared in a first step in which a diluted choline hydroxide solution is made by reacting ethylene oxide with TMA in an excess of water. In a second step the dilute choline hydroxide solution was evaporated to form a concentrated choline hydroxide solution. The sample was pumped continuously at a rate of 200 ml/h into a laboratory wiped film evaporator. A vacuum of 35 mbar was applied and the evaporation was performed at a temperature of 90° C. No stabilizer was added to the sample either during synthesis or prior to evaporation. In this way, an aqueous choline hydroxide solution was obtained of 45% w by concentration. The colour evolved from pale yellow to yellow, corresponding to the increase of the concentration. There was no significant evidence of formation of additional colour in the samples.

Example 5

Showing Increasing Competition of O-Ethoxylation Over N-Ethoxylation at Increasing Choline Hydroxide Concentrations in a Single Phase Fed Batch Reactor Water (4000 g) and TMA (1680 g) were loaded to a 20 liter STR (stirred tank reactor) reactor. EO (ethylene oxide, 1416 g) was fed at such a rate that the EO in the gas cap did not exceed the concentration of 10% V/V (this typically takes about 4 to 6 hours). During the course of the fed batch reaction, the temperature was controlled between 35-40° C. Consecutive samples were taken over the reaction course and analyzed. The results are shown in Table 5.

TABLE 5

| EO fed (g) | Residual TMA (% wt) | Choline Hydroxide (% wt) | Higher Ethoxylates (% wt) |
|---|---|---|---|
| 627 | 8.64 | 28.7 | 0.63 |
| 940 | 2.75 | 38.8 | 1.84 |
| 1128 | 1.13 | 42.7 | 3.40 |
| 1253 | 0.61 | 43.5 | 5.54 |
| 1316 | 0.38 | 43.0 | 7.33 |
| 1416 | 0.24 | 41.9 | 9.52 |

These results show that as the TMA concentration reduces and the cbase concentration in the reaction medium increases, the competition between the N-ethoxylation and the O-ethoxylation reaction moves towards the formation of more O-ethoxylated by-products.

Example 6

Showing Phase Separation Between Choline Hydroxide/Water and TMA at High Choline Hydroxide Concentration An aqueous solution of 45% wt choline hydroxide was by thermostat kept at a temperature of 60° C. and stirred in a pressure resistant glass reactor. Liquid TMA was added to the liquid phase until two phases were clearly observed. When stirring was stopped, two clear layers were formed within one minute. The choline hydroxide layer was sampled and found to contain 2% of TMA. This would correspond with a molar excess of TMA of approximately 9%. Thus, when an excess of TMA is used that is higher than 9% molar, two phases may be formed.

Example 7

To 97.6 parts by weight of a 15% wt aqueous solution of trimethylamine, 7.25 parts of ethylene oxide was added while the temperature was kept at 60° C. The mixture was stirred until the reaction was substantially complete, keeping the temperature fixed at 60° C. Unreacted TMA and excess water was removed under a vacuum of 120 mbar absolute pressure and at a temperature in the range of 40-50° C., until a concentrated choline hydroxide (cbase) solution at about 45% wt cbase was obtained. The concentrated cbase solution contained only 1.93% wt of O-ethoxylation by-products.

Although the invention is illustrated and described herein with reference to specific embodiments, the invention is not intended to be limited to the details shown. Rather, various modifications may be made in the details within the scope and range of equivalents of the claims and without departing from the invention.

The invention claimed is:

1. A process for the production of choline hydroxide comprising:
   a) reacting at a temperature above 35° C., in the presence of an aqueous medium, primary reactants comprising ethylene oxide, trimethylamine, and water in such amounts as to form a diluted choline hydroxide solution having a choline hydroxide concentration of at most 38.0 wt %, and
   b) removing at least a portion of the aqueous medium from the diluted choline hydroxide solution to form a concentrated aqueous choline hydroxide solution having a choline hydroxide concentration which is at least 1.05 times the choline hydroxide concentration of the diluted choline hydroxide solution.

2. The process according to claim 1, wherein the aqueous medium comprises a molar excess of water of 100% to 6000% relative to the stoichiometric amount theoretically required for forming the amount of choline hydroxide in the diluted choline hydroxide solution.

3. The process according to claim 1, wherein a molar excess of trimethylamine is used when reacting the ethylene oxide, trimethylamine, and water.

4. The process according to claim 3, wherein the molar excess of trimethylamine is in the range of 5% to 200% excess trimethylamine relative to the stoichiometric amount required for forming the amount of choline hydroxide in the diluted choline hydroxide solution.

5. The process according to claim 3, wherein excess trimethylamine is removed from the diluted choline hydroxide solution or from the concentrated choline hydroxide solution.

6. The process according to claim 1, wherein the diluted choline hydroxide solution comprises choline hydroxide at a concentration of 10% to 38.0% by weight, based on the total weight of the diluted choline hydroxide solution.

7. The process according to claim 1, wherein the primary reactants are in step a) reacted at a temperature of at most 150° C.

8. The process according to claim 1, wherein the concentrated aqueous choline hydroxide solution has a choline hydroxide concentration which is at least 1.10 times the choline hydroxide concentration of the diluted choline hydroxide solution formed in step a).

9. The process according to claim 1, wherein the aqueous medium is at least partially removed from the diluted choline hydroxide solution by at least one of evaporation, stripping, membrane based separation, and combinations thereof.

10. The process according to claim 9, wherein the aqueous medium is at least partially removed from the diluted choline hydroxide solution by evaporation and wherein the evaporation is at least partly being performed under vacuum.

11. The process according to the claim 9, wherein the aqueous medium is at least partially removed from the diluted choline hydroxide solution by evaporation and wherein the evaporation is followed by at least partial condensation of the evaporated water and possibly present evaporated trimethylamine.

12. The process according to claim 11, further comprising the step of recycling at least part of the condensed water to step a).

13. The process according to claim 1, wherein the concentrated aqueous choline hydroxide solution comprises choline hydroxide at a concentration of 30% to 60% by weight, based on total weight of the concentrated choline hydroxide solution.

14. The process according to claim 1, wherein the concentrated aqueous choline hydroxide solution comprises a stabiliser.

15. The process according to claim 14, wherein the stabiliser comprises at least one of dithionite salts, amines, more particular hydroxylamines, sulphites, hydroquinones, hydrides, carboxylic acids, piperazines, and mixtures thereof.

16. The process according to claim 1, which is performed in continuous mode.

17. The process according to claim 1, whereby the reaction is performed in at least one loop reactor.

18. The process according to claim 1, whereby the reaction is performed in at least two reactors in series.

19. The process according to claim 18, whereby the reaction is performed in three reactors in series.

20. The process according to claim 18, wherein the ethylene oxide addition is split and divided over more than one of the reactors.

21. The process according to claim 1, wherein the water added to step a) is at least partly comprising water having a total metal concentration which is at most 5.0 ppm by weight.

22. The process according to claim 21, whereby in the water added to step a) is at least partly comprising water of which the total content of the metals belonging to the group consisting of Fe, Cr, Na, Al, Ca, Cu, K, Mg, Mn, Pb and Zn is at most 1000 ppb.

23. The process according to claim 1, wherein the trimethylamine is produced by the reaction of methanol and ammonia.

24. The process according to claim 23, wherein the trimethylamine is produced by the reaction of methanol and ammonia over a solid acid catalyst.

25. The process according to claim 24, wherein the solid acid catalyst is a silica-alumina catalyst.

26. The process according to claim 25, wherein the silica-alumina catalyst is a catalyst selected from an amorphous silica-alumina catalyst and a shape-selective zeolite catalyst.

27. The process according to claim 1, further comprising the step of using the concentrated choline hydroxide from step b) for the neutralisation of an acid compound.

28. The process according to claim 27, wherein the acid compound is in a formulation.

29. The process according to claim 28, wherein the formulation is a formulation selected from a detergent formulation, an agrochemical formulation, and combinations thereof.

30. The process according to claim 1, further comprising the step of reacting the choline hydroxide from step a) or from step b) to form an ionic surfactant.

31. The process according to claim 30, wherein the ionic surfactant is a surfactant having the formula R-A-$SO_3$—[$(H_3C)_3$N—$CH_2$—$CH_2$—OH]$^+$, whereby A represents an oxygen atom or a group having the formula —[O-B]$_n$-O—, whereby B represents an alkyl group having 2 to 4 carbon atoms and n represents an integer in the range of 1-20, and R represents a saturated or unsaturated, unbranched or branched alkyl group having from 8 to 30 carbon atoms.

* * * * *